United States Patent [19]

Panzer

[11] Patent Number: 4,731,379

[45] Date of Patent: Mar. 15, 1988

[54] FLEA ERADICATOR

[75] Inventor: Jack S. Panzer, Detroit, Mich.

[73] Assignee: H.S.C. Corporation, Detroit, Mich.

[21] Appl. No.: 741,431

[22] Filed: Jun. 5, 1985

Related U.S. Application Data

[63] Continuation-in-part of Ser. No. 558,978, Dec. 7, 1983, abandoned.

[51] Int. Cl.$^4$ ...................... A01N 37/02; A01N 65/00
[52] U.S. Cl. .................................. 514/547; 424/195.1; 424/DIG. 10; 514/829; 514/919
[58] Field of Search ..................... 424/195.1, DIG. 10; 514/547, 829, 919

[56] References Cited

U.S. PATENT DOCUMENTS 2,871,158  1/1959  Cardaciotto et al. ............... 514/547

OTHER PUBLICATIONS

Merck Index, 9th ed. 1976, No. 3288.

*Primary Examiner*—J. R. Brown
*Assistant Examiner*—John W. Rollins, Jr.
*Attorney, Agent, or Firm*—Gifford, Groh, VanOphem, Sheridan, Sprinkle and Dolgorukov

[57] ABSTRACT

A flea eradicator consists essentialy of 1.7 percent by weight dioctyl sodium sulfosuccinate and 0.3 percent by weight sodium benzoate in water. The composition is topically applied and kills fleas substantially more quickly than do conventional flea soaps. The use of dioctyl sodium sulfosuccinate avoids thre problems of malodorous soaps, toxic insecticides and alkalin harshness usually associated with flea soaps. The need to incorporate polyethylene glycol or lanolin in the flea eradicator is thereby eliminated, as is the need for any other toxic insecticide. The use of sodium benzoate appears to promote healing of the infested area.

13 Claims, No Drawings

FLEA ERADICATOR

CROSS-REFERENCE

This application is a continuation-in-part application of U.S. Ser. No. 558,978, filed Dec. 7, 1983, now abandoned entitled FLEA ERADICATOR.

BACKGROUND OF THE INVENTION

I. Field of the Invention

The present invention is directed to compositions for eradicating vermin, and more particularly to topically applicable flea eradicators.

II. Description of the Prior Art

Flea soaps have long been known for killing fleas which have infested the fur of an animal, for example, a house pet such as a dog or a cat. Typically, flea soaps comprise a soap, an insecticide and either polyethylene glycol or lanolin. Soaps, of course, are water-soluble reaction products of a fatty acid ester and an alkali (usually sodium hydroxide), with glycerol as a by-product. Soaps are generally alkaline, rather than neutral or acidic, and have a pH of about 9.5 to 10.0. This alkalinity is known to have the effect of decreasing the moisture in, and thereby drying out, the skin. Inflea soaps, polyethylene glycol or lanolin is added to the soap and insecticide to reduce the effects to the animal or the user of such alkalinity.

While the known flea soaps are useful for their intended purpose, their use has several drawbacks. Many flea soaps are malodorous due to their constituents. The toxicity of the insecticide can render the product dangerous to both the animal and user. Moreover, there is a harshness to the skin of both the animal and the user associated with the soaps conventionally employed in flea soaps. Finally, flea soaps generally require prolonged foaming or lathering for optimum effectiveness. Usually such lathering must occur for at least a few minutes, generally with vigorous scrubbing activity.

BRIEF DESCRIPTION OF THE PRESENT INVENTION

The present invention overcomes these and other drawbacks of prior flea soaps by providing a quick-acting yet nontoxic flea eradicator. The flea eradicator according to the present invention consists essentially of dioctyl sodium sulfosuccinate in an appropriate carrier. Preferably, the flea eradicator according to the present invention comprises a solution of about 1.7 per cent dioctyl sodium sulfosuccinate and 0.3 per cent sodium benzoate by weight in distilled water. This composition is particularly advantageous in that, despite the anionic nature of the diocyl sodium sulfoccinate, the composition is relatively neutral as compared to conventional flea soaps. No additional agent such as polyethyleneglycol or lanolin is required to offset the alkaline harshness experienced wtih other flea killers. Moreover, dioctyl sodium sulfosuccinate and sodium benzoate are generally nontoxic, so that any threat to the health of the animal or the user is avoided. They have no offensive odor and are, therefore, more pleasant to use than are many conventional flea soaps. The use of sodium benzoate appears to assist the healing of previous inflammation of the skin in the infected area after treatment. Finally, the preferred composition acts substantially more quickly to kill fleas than do the known flea soaps.

The method of killing fleas according to the present invention comprises the topical application of an effective amount of dioctyl sodium sulfosuccinate to a flea-infested area of mammalian skin, preferably an effective amount of the preferred composition identified above. Generally, one or two ounces of the preferred composition are sufficient to eradicate the fleas from an average sized dog. This method is particularly convenient because the composition does not need to be rinsed from the animal, thus avoiding the need for the water, basins and handling problems usually associated with treating flea infestation in animals. Preferably, the composition is not rinsed from the animal, but is permitted to remain on the infested area. This is allowed by the nontoxic nature of its constituents.

DETAILED DESCRIPTION OF THE PREFERRED EMBODIMENT OF THE PRESENT INVENTION

The flea eradicating composition according to the present invention consists essentially of dioctyl sodium sulfosuccinate. Dioctyl sodium sulfosuccinate is a known surfactant having the formula $C_8H_{17}OOCCH_2CH(SO_3Na)COOC_8H_{17}$. Preferably, the dioctyl sulfosuccinate is combined in aqueous solution with sodium benzoate, for the antifungal properties of the latter. A combination of the two is available from American Cyanamid Co., Wayne, N.J., under the name "OTB", suplied as a powder comprising 85 per cent by weight dioctyl sodium sulfosuccinate, and 15 per cent by weight sodium benzoate. By itself, sodium benzoate is known to be useful as a food preservative. Dioctyl sodium sulfosuccinate is available for other purposes as well; for example, as an over the counter, nontoxic stool softener sold under the name "Cholase".

Preferably, the dioctyl sodium sulfosuccinate and sodium benzoate are combined in an appropriate carrier, to facilitate their application to the flea infested area of the animal. This carrier can be either physiologically active or inert, so long as it does not interfere with the effectiveness of the dioctyl sodium sulfosuccinate. In the particularly preferred embodiment, the composition consists essentially of two (2%) per cent "OTB" by weight in distilled water.

The method of eradicating fleas according to the present invention employs the composition and is straightforward. The composition is topically applied to the flea-infested area of the animal or to the entire animal. Preferably, the composition is not rinsed from the animal after application, but is allowed to remain on it in order to assist the healing of the rash and redness of the skin usually associated with flea infestation. For example, generally about one or two ounces of the preferred composition are sufficient to eradicate the typical flea infestation in an average sized dog.

The following example is illustrative of the present invention:

EXAMPLE

Two (2%) per cent by weight "OTB" is dissolved in distilled water. This solution thus contains 1.7 per cent by weight dioctyl sodium sulfosuccinate and 0.3 per cent by weight sodium benzoate. A quantity of the solution is applied to the animal, in an amount sufficient to eradicate the fleas infesting the area in which the solution is applied. About 1 to 2 ounces are applied to the average dog. The eradicating effect of the solution will be almost immediately observed. Within a few seconds of the application of the composition to the dog, for example, the fleas in the infested area are killed. The solution is not rinsed from the animal, but is allowed to remain on it. The effect obtained by the composition of the present invention is complete for that bout of infestation, that is, a second application of the composition is not necessary to insure complete eradication of the infestation.

Advantages of the present invention abound. The time for eradication of fleas to occur when the present composition is employed is substantially less than the few or several minutes usually necessary to observe results from the application of conventional flea soaps. The composition according to the present invention appears to be effective in clearing the rash and redness associated with flea infestation, perhaps due in part to the relative neutrality of the composition with respect to the soap contained in conventional flea soaps, and in the preferred embodiment, to the inclusion of sodium benzoate. The use of dioctyl sodium sulfosuccinate avoids the need to include a malodorous soap or insecticide, and avoids the toxicity problems associated with an insecticide as well, since these materials are preferably omitted. Because of the relative neutrality of the composition of the present invention, the alkaline harshness associated with other flea soaps is not experienced. Also because of this relative neutrality, the composition does not require the inclusion of polyethylene glycol or lanolin as additives. This results in a flea killer which is less chemically complex, and therefore quicker and less expensive to manufacture, than are other known flea eradicators. Finally, the use of dioctyl sodium sulfosuccinate results in a flea eradicating composition which requires substantially less time to act than do conventional flea soaps, and which provides a healing rather than irritating effect. The period of application is reduced to a few seconds, from the few or several minutes which have been typically necessary.

Of course, it should be obvious to one skilled in the art that other excipients or carriers may be used in the present invention, instead of distilled water. Perfumes and other adjuvants can be added. Aloe vera is one such adjuvant or perfume whose addition falls well within the scope of the present invention. Aloe vera is a well known extract from plants of the genus Aloe, which are mostly native to southern Africa, and which have fleshy, spiney toothed leaves and red or yellow flowers. Alternatively, it is expected that the dioctyl sodium sulfosuccinate and sodium benzoate need not be combined in a water solution, but could be prepared as a (preferably water soluble or dispersible) cream or solid material. Conveniently, however, the composition can comprise an aqueous solution having a concentration of dioctyl sodium sulfosuccinate of about at least 0.1 per cent by weight. The selection of the protocol necessary to prepare such other embodiments should be easily discernible by one skilled in the art, in light of my disclosure.

Having described my invention, however, many modifications thereto will become apparent to one skilled in the art to which it pertains, without deviation from the spirit of the present invention, as defined by the scope of the appended claims.

I claim:

1. A composition for the eradication of flea infestation of mammalian skin, adapted for topical application to said infested area of skin, said composition consisting essentially of about 1.7 per cent by weight dioctyl sodium sulfosuccinate and about 0.3 per cent by weight sodium benzoate in water.

2. The composition according to claim 1, wherein said composition is substantially free of any insecticide or soap which is effective against flea infestation.

3. A method for the eradication of fleas from an infested area of mammalian skin, comprising the topical application to said area of an effective amount of the composition according to claim 2.

4. The composition according to claim 1, wherein said composition is substantially free of lanolin and polyethylene glycol.

5. A method for the eradication of fleas from an infested area of mammalian skin, comprising the topical application to said area of an effective amount of the composition according to claim 4.

6. The composition according to claim 1, wherein said composition is substantially free of any alkalinity-offsetting constituent.

7. A method for the erradication of fleas from an infested area of mammalian skin, comprising the topical application to said area of an effective amount of the composition according to claim 6.

8. A method for the eradication of fleas from an infested area of mammalian skin, comprising the topical application to said area of an effective amount of the composition according to claim 1.

9. A method for the eradication of fleas from an infested area of mammalian skin, comprising the topical application to said area of an effective amount of dioctyl sodium sulfosuccinate.

10. A method for the eradication of fleas from an infested area of mammalian skin, comprising the topical application to said area of an effective amount of dioctyl sodium sulfosuccinate in a physiologically acceptable carrier, wherein said method comprises the topical application of a solution of at least 0.1 per cent by weight dioctyl sodium sulfosuccinate in water.

11. The method according to claim 10, wherein said composition is substantially free of any insecticide or soap which is effective against flea infestation.

12. The method according to claim 10, wherein said composition is substantially free of lanolin and polyethylene glycol.

13. The method according to claim 10, wherein said composition is substantially free of any alkalinity-offsetting constituent.

* * * * *